(12) United States Patent
Masson et al.

(10) Patent No.: US 9,446,240 B2
(45) Date of Patent: *Sep. 20, 2016

(54) SYSTEM AND METHOD FOR NEUROMODULATION

(71) Applicant: Interventional Autonomics Corporation, Chapel Hill, NC (US)

(72) Inventors: Stephen C Masson, Raleigh, NC (US); Terrance Ransbury, Chapel Hill, NC (US); Richard S Stack, Chapel Hill, NC (US); William E Sanders, Chapel Hill, NC (US)

(73) Assignee: INTERVENTIONAL AUTONOMICS CORPORATION, Chapel Hill, NC (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/516,734

(22) Filed: Oct. 17, 2014

(65) Prior Publication Data

US 2015/0039058 A1 Feb. 5, 2015

Related U.S. Application Data

(63) Continuation of application No. 13/547,031, filed on Jul. 11, 2012, now Pat. No. 9,067,071.

(60) Provisional application No. 61/506,164, filed on Jul. 11, 2011, provisional application No. 61/551,418, (Continued)

(51) Int. Cl.
*A61N 1/36* (2006.01)
*A61N 1/05* (2006.01)

(52) U.S. Cl.
CPC ........... *A61N 1/36114* (2013.01); *A61N 1/056* (2013.01); *A61N 1/0551* (2013.01); *A61N 1/36053* (2013.01); *A61N 1/36135* (2013.01); *A61N 1/36139* (2013.01)

(58) Field of Classification Search
CPC .......................... A61N 1/36114; A61N 1/056
See application file for complete search history.

(56) References Cited

U.S. PATENT DOCUMENTS

| 4,240,433 A | 12/1980 | Bordow |
| 5,154,172 A | 10/1992 | Terry, Jr. |

(Continued)

FOREIGN PATENT DOCUMENTS

| WO | WO 2005/065771 A1 | 7/2005 |
| WO | WO 2006/122148 A2 | 11/2006 |

(Continued)

OTHER PUBLICATIONS

Bilgutay et al, Vagal Tuning: a new concept in the treatment of supraventricular arrhythmias, angina pectoris, and heart failure, Journal of Thoracic of Cardiovascular Surgery, 1968, vol. 56, No. 1, 71-82.

(Continued)

*Primary Examiner* — Michael Kahelin (57) ABSTRACT

A method of treating autonomic imbalance in a patient includes energizing a first therapeutic element disposed to deliver therapy to a parasympathetic nerve fiber (e.g. vagus nerve), and energizing a second therapeutic element to deliver therapy to a sympathetic cardiac nerve fiber. At least one of the therapeutic elements is disposed in the vasculature superior to the heart. The therapy decreases the patient's heart rate and elevates or maintains the blood pressure of the patient.

13 Claims, 4 Drawing Sheets

Related U.S. Application Data filed on Oct. 25, 2011, provisional application No. 61/548,812, filed on Jan. 9, 2012, provisional application No. 61/601,501, filed on Feb. 21, 2012, provisional application No. 61/613,433, filed on Mar. 20, 2012, provisional application No. 61/639,982, filed on Apr. 29, 2012.

(56) References Cited

U.S. PATENT DOCUMENTS

| | | | |
|---|---|---|---|
| 5,179,950 | A | 1/1993 | Stanislaw |
| 5,269,303 | A | 12/1993 | Wernicke |
| 5,304,206 | A | 4/1994 | Baker, Jr. |
| 5,531,779 | A | 7/1996 | Dahl |
| 5,628,779 | A | 5/1997 | Bornzin et al. |
| 5,651,378 | A | 7/1997 | Matheny |
| 5,700,282 | A | 12/1997 | Zabara |
| 5,707,400 | A | 1/1998 | Terry, Jr. |
| 5,913,876 | A | 6/1999 | Taylor |
| 5,928,272 | A | 7/1999 | Adkins |
| 5,954,761 | A | 9/1999 | Machek |
| 6,181,966 | B1 | 1/2001 | Nigam |
| 6,292,695 | B1 | 9/2001 | Webster, Jr. |
| 6,429,217 | B1 | 8/2002 | Pkas |
| 6,445,953 | B1 | 9/2002 | Bulkes |
| 6,449,507 | B1 | 9/2002 | Hill |
| 6,473,644 | B1 | 10/2002 | Terry, Jr. |
| 6,479,523 | B1 | 11/2002 | Pkas |
| 6,522,926 | B1 | 2/2003 | Kieval |
| 6,529,779 | B1 | 3/2003 | Sutton |
| 6,542,774 | B2 | 4/2003 | Hill |
| 6,564,096 | B2 | 5/2003 | Mest |
| 6,616,624 | B1 | 9/2003 | Kieval |
| 6,622,041 | B2 | 9/2003 | Terry, Jr. |
| 6,656,960 | B2 | 12/2003 | Pkas |
| 6,690,971 | B2 | 2/2004 | Schauerte |
| 6,697,676 | B2 | 2/2004 | Dahl |
| 6,721,603 | B2 | 4/2004 | Zabara |
| 6,748,272 | B2 | 6/2004 | Carlson |
| 6,778,854 | B2 | 8/2004 | Pkas |
| RE38,705 | E | 2/2005 | Hill |
| 6,850,801 | B2 | 2/2005 | Kieval |
| 6,885,888 | B2 | 4/2005 | Rezai |
| 6,907,285 | B2 | 6/2005 | Denker |
| 6,912,419 | B2 | 6/2005 | Hill |
| 6,934,583 | B2 | 8/2005 | Weinberg |
| 6,937,896 | B1 | 8/2005 | Kroll |
| 6,978,174 | B2 | 12/2005 | Gelfand |
| 6,985,774 | B2 | 1/2006 | Kieval |
| 7,069,070 | B2 | 6/2006 | Carlson |
| 7,072,720 | B2 | 7/2006 | Puskas |
| 7,110,828 | B2 | 9/2006 | Kolberg |
| 7,123,959 | B2 | 10/2006 | Cates |
| 7,123,961 | B1 | 10/2006 | Kroll |
| 7,139,607 | B1 | 11/2006 | Shelchuk |
| 7,142,917 | B2 | 11/2006 | Fukui |
| 7,149,574 | B2 | 12/2006 | Yun |
| 7,162,303 | B2 | 1/2007 | Levin |
| 7,181,288 | B1 | 2/2007 | Rezai |
| 7,184,829 | B2 | 2/2007 | Hill |
| 7,194,313 | B2 | 3/2007 | Libbus |
| 7,225,019 | B2 | 5/2007 | Jahns |
| 7,231,260 | B2 | 6/2007 | Wallace |
| 7,269,457 | B2 | 9/2007 | Shafer |
| 7,277,761 | B2 | 10/2007 | Shelchuk |
| 7,299,091 | B2 | 11/2007 | Barrett |
| 7,310,552 | B2 | 12/2007 | Pkas |
| 7,330,765 | B2 | 2/2008 | Haldeman |
| 7,336,997 | B2 | 2/2008 | Fukui |
| 7,340,299 | B2 | 3/2008 | Pkas |
| 7,363,076 | B2 | 4/2008 | Yun |
| 7,386,345 | B2 | 6/2008 | Pastore |
| 7,455,753 | B2 | 11/2008 | Roth |
| 7,477,945 | B2 | 1/2009 | Rezai |
| 7,485,104 | B2 | 2/2009 | Kieval |
| 7,486,991 | B2 | 2/2009 | Libbus |
| 7,499,744 | B2 | 3/2009 | Carlson |
| 7,499,748 | B2 | 3/2009 | Moffitt |
| 7,509,166 | B2 | 3/2009 | Libbus |
| 7,519,421 | B2 | 4/2009 | Denker |
| 7,519,424 | B2 | 4/2009 | Dennis |
| 7,532,938 | B2 | 5/2009 | Machado |
| 7,555,341 | B2 | 6/2009 | Moffitt |
| 7,555,351 | B2 | 6/2009 | Zhang |
| 7,561,923 | B2 | 7/2009 | Libbus |
| 7,572,226 | B2 | 8/2009 | Scheiner |
| 7,596,413 | B2 | 9/2009 | Libbus |
| 7,617,003 | B2 | 11/2009 | Caparso |
| 7,617,005 | B2 | 11/2009 | Demarais |
| 7,620,451 | B2 | 11/2009 | Demarais |
| 7,634,317 | B2 | 12/2009 | Ben-David |
| 7,643,875 | B2 | 1/2010 | Heil, Jr. |
| 7,647,114 | B2 | 1/2010 | Libbus |
| 7,647,115 | B2 | 1/2010 | Levin |
| 7,653,438 | B2 | 1/2010 | Deem |
| 7,676,275 | B1 | 3/2010 | Farazi |
| 7,717,948 | B2 | 5/2010 | Demarais |
| 7,747,323 | B2 | 6/2010 | Libbus |
| 7,756,583 | B2 | 7/2010 | Demarais |
| 7,765,000 | B2 | 7/2010 | Zhang |
| 7,769,446 | B2 | 8/2010 | Moffitt |
| 7,769,470 | B1 | 8/2010 | Rezai |
| 7,778,704 | B2 | 8/2010 | Rezai |
| 7,778,711 | B2 | 8/2010 | Ben-David |
| 7,783,362 | B2 | 8/2010 | Whitehurst |
| 7,801,627 | B2 | 9/2010 | Haldeman |
| 7,809,447 | B2 | 10/2010 | Dreier |
| 7,813,812 | B2 | 10/2010 | Kieval |
| 7,833,164 | B2 | 11/2010 | Scheiner |
| 7,840,278 | B1 | 11/2010 | Pkas |
| 7,853,333 | B2 | 12/2010 | Demarais |
| 7,865,237 | B2 | 1/2011 | Machado |
| 7,865,249 | B2 | 1/2011 | Reddy |
| 7,869,881 | B2 | 1/2011 | Libbus |
| 7,873,417 | B2 | 1/2011 | Demarais |
| 7,877,146 | B2 | 1/2011 | Rezai |
| 7,881,788 | B2 | 2/2011 | Fukui |
| 7,885,711 | B2 | 2/2011 | Ben-Ezra |
| 7,890,187 | B2 | 2/2011 | Hochareon |
| 7,890,188 | B2 | 2/2011 | Zhang |
| 7,904,175 | B2 | 3/2011 | Scott |
| 7,917,230 | B2 | 3/2011 | Bly |
| 7,937,143 | B2 | 5/2011 | Demarais |
| 7,949,409 | B2 | 5/2011 | Bly |
| 7,962,214 | B2 | 6/2011 | Byerman |
| 8,024,050 | B2 | 9/2011 | Libbus |
| 8,032,215 | B2 | 10/2011 | Libbus |
| 8,046,075 | B2 | 10/2011 | Rezai |
| 8,126,560 | B2 | 2/2012 | Scheiner |
| 8,412,350 | B2 | 4/2013 | Bly |
| 2002/0120304 | A1 | 8/2002 | Mest |
| 2003/0004549 | A1 | 1/2003 | Hill |
| 2003/0229380 | A1 | 12/2003 | Adams |
| 2004/0019364 | A1 | 1/2004 | Kieval |
| 2004/0176672 | A1 | 9/2004 | Silver |
| 2005/0096710 | A1 | 5/2005 | Kieval |
| 2005/0149156 | A1 | 7/2005 | Libbus |
| 2005/0251238 | A1 | 11/2005 | Wallace |
| 2005/0251239 | A1 | 11/2005 | Wallace |
| 2006/0079945 | A1 | 4/2006 | Libbus |
| 2006/0229677 | A1 | 10/2006 | Moffitt |
| 2006/0253161 | A1 | 11/2006 | Libbus et al. |
| 2007/0129763 | A1 | 6/2007 | Cates |
| 2007/0142879 | A1 | 6/2007 | Greenberg |
| 2007/0191904 | A1 | 8/2007 | Libbus |
| 2007/0282412 | A1 | 12/2007 | Soltis |
| 2007/0282414 | A1 | 12/2007 | Soltis |
| 2007/0288076 | A1 | 12/2007 | Bulkes |
| 2007/0293925 | A1 | 12/2007 | Zarembo |
| 2008/0009917 | A1 | 1/2008 | Rossing |
| 2008/0183259 | A1 | 7/2008 | Bly |
| 2008/0183264 | A1 | 7/2008 | Bly |
| 2008/0234779 | A1 | 9/2008 | Pedersen |
| 2008/0288017 | A1 | 11/2008 | Kieval |

(56) References Cited

U.S. PATENT DOCUMENTS

| | | |
|---|---|---|
| 2008/0312712 A1 | 12/2008 | Penner |
| 2009/0005859 A1 | 1/2009 | Keilman |
| 2009/0030331 A1 | 1/2009 | Hochareon et al. |
| 2009/0036940 A1 | 2/2009 | Wei |
| 2009/0155336 A1 | 6/2009 | Rezai |
| 2009/0171411 A1 | 7/2009 | Machado |
| 2009/0228078 A1 | 9/2009 | Zhang |
| 2009/0248119 A1 | 10/2009 | Libbus |
| 2009/0275956 A1 | 11/2009 | Burnes et al. |
| 2009/0275997 A1 | 11/2009 | Faltys |
| 2009/0276025 A1 | 11/2009 | Burnes |
| 2009/0318989 A1 | 12/2009 | Tomaschko |
| 2010/0036451 A1 | 2/2010 | Hoffer |
| 2010/0100151 A1 | 4/2010 | Terry, Jr. |
| 2010/0113890 A1 | 5/2010 | Cho |
| 2010/0114254 A1 | 5/2010 | Kornet |
| 2010/0137949 A1 | 6/2010 | Mazgalev |
| 2010/0191304 A1 | 7/2010 | Scott |
| 2010/0204741 A1 | 8/2010 | Tweden |
| 2010/0222832 A1 | 9/2010 | Zhang |
| 2011/0029037 A1 | 2/2011 | Rezai |
| 2011/0098762 A1 | 4/2011 | Rezai |
| 2011/0152877 A1 | 6/2011 | Bly |
| 2011/0152974 A1 | 6/2011 | Rezai |

FOREIGN PATENT DOCUMENTS

| | | | |
|---|---|---|---|
| WO | WO 2007/075593 A1 | 7/2007 | |
| WO | WO 2008/070189 A2 | 6/2008 | |
| WO | WO 2008/092246 A1 | 8/2008 | |
| WO | WO 2009/075750 A2 | 6/2009 | |
| WO | WO 2010/174571 | 2/2010 | |

OTHER PUBLICATIONS

Cooper et al, Neural effects on sinus rate and atrioventricular conduction produced by electrical stimulation from a transvenous electrode catheter in the canine right pulmonary artery, Circ. Res. 1980; 46; 48-57.

Koizumi et al, Function significance of coactivation of vagal and sympathetic cardiac nerves, Proc. Natl. Acad. Sci., USA, (1982) 79: 2116-2120.

Bernston et al, Autonomic Determinism: The Modes of Autonomic Control, the Doctrine of Autonomic Space, and the Laws of Autonomic Constraint, Psychological Review, 1991, vol. 98, No. 4, 459-487.

Carlson et al, Selective Stimulation of Parasympathetic Nerve Fibers to the Human SA Node, Circulation, 1992: 85: 1311-1317.

Yang et al, Sequence of excitation as a factor in sympathetic-parasympathetic interactions in the heart, Circ. Res., 1992, 71: 898-905.

Thompson, Bradycardia Induced by Intravascular Versus Direct Stimulation of the Vagus Nerve, Ann Thorac. Surg, 1998, 65: 637-42.

Schuarte et al, Ventricular Rate Control During Atrial Fibrillation by Cardiac Parasympathetic Nerve Stimulation: A Transvenous Approach, Journal of the American College of Cardiology, vol. 34, No. 7 (Dec. 1999) p. 2043-50.

Schuarte et al, Catheter Stimulation of Cardiac Parasympathetic Nerves in Humans: A Novel Approach to the Cardiac ANS, Circulation 2001, 104: 2430-2435.

Kawashima et al, The autonomic nervous system of the human heart with special reference to its origin, course, and peripheral distribution, Anat Embryol, 2005, 209: 425-438.

Paton et al, The yin and yang of cardiac autonomic control: Vago-sympathetic interactions revisited, Brain Research Reviews, 2005, 49(3): 555-65.

Berntson et al, Cardiac autonomic balance versus cardiac regulatory capacity, Psychophysiology, 2008, 45: 643-652.

Olshansky, et al, Parasympathetic Nervous System and Heart Failure: Pathophysiology and Potential Implications for Therapy, Circulation 2008, 118: 863-871.

Meyer et al, Augmentation of Left Ventricular Contractility by Cardiac Sympathetic Neural Stimulation, Circ. Res., 2010, 121: 1286-1294.

Brown et al, Long term bradycardia by electrical pacing: a new method for studying heart rate reduction, Cardiovascular Research, 1994; 28: 1774-1779.

Goldberger et al, New technique for vagal nerve stimulation, Journal of Neuroscience Methods 91 (1999), 109-114.

Li et al, Vagal Nerve Stimulation Markedly Improves Long-Term Survival After Chronic Heart Failure in Rats, Circulation 2004; 109-120-124.

Schwartz et al, Long term vagal stimulation in patients with advanced heart failure. First experience in man., European Journal of Heart Failure 10(2008) 884-891.

Nabutovsky et al, Lead Design and Initial Applications of a New Lead for Long-Term Endovascular Vagal Stimulation, PACE, vol. 30, S215-S218. 2007.

Janes, Anatomy of Human Extrinsic Cardiac Nerves and Ganglia, Am. J. Cardiol 1986; 57:299-309.

Kobayashi et al, Effect of Epivascular Cardiac Autonomic Nerve Stimulation Anatomy on Cardiac Function, Ann. Thorac. Surg. 94: 1150-6, Oct. 2012.

SYSTEM AND METHOD FOR NEUROMODULATION

PRIORITY

This application is a continuation of U.S. application Ser. No. 13/547,031, (now U.S. Pat. No. 9,067,071) filed Jul. 11, 2012, which claims the benefit of U.S. Provisional Application No. 61/506,164, filed Jul. 11, 2011, U.S. Provisional Application No. 61/551,418, filed Oct. 25, 2011, U.S. Provisional Application No. 61/584,812, filed Jan. 9, 2012, U.S. Provisional Application No. 61/601,501, filed Feb. 21, 2012, U.S. Provisional Application No. 61/613,433, filed Mar. 20, 2012, and U.S. Provisional Application No. 61/639,982, filed Apr. 29, 2012. Each of the foregoing applications is incorporated herein by reference.

TECHNICAL FIELD OF THE INVENTION

The present application generally relates to systems and methods for neuromodulation using stimulation elements disposed within the vasculature.

BACKGROUND

Acute heart failure syndromes (AHFS) are serious conditions resulting in millions of hospitalizations each year. Well documented in the literature are causal links between declining renal function or myocardial injury during AHFS hospitalization and poor prognosis. Heart failure resulting from myocardial ischemic insult or tachycardia precipitates complex alterations in autonomic tone, neurohormonal activation, and the inflammatory metabolic state. These changes in autonomic tone are typically manifested by increased heart rate and a reduction in heart rate variability. In the setting of an acute exacerbation of heart failure, the dramatically elevated heart rate is frequently accompanied by hypotension. The critical role of treating the autonomic nervous system dysfunction observed in HF has long been recognized (with inotropic agents and beta-blockers). Recently, specific neuromodulation of the parasympathetic cardiac nerve inputs has shown significant therapeutic benefit. Cleland J G, Bristow M R, Erdmann E, Remme W J, Swedberg K, Waagstein F. *Beta-blocking agents in heart failure. Should they be used and how?* Eur Heart J 1996; 17:1629-39; De Ferrari G M, Crijns H J, Borggrefe M, et al. *Chronic vagus nerve stimulation: a new and promising therapeutic approach for chronic heart failure.* Eur Heart J 2011; 32:847-55.

However, in the case of AHFS associated with congestive symptoms and reduced blood pressure (BP), the negative inotropic effects of lone parasympathetic intervention or beta-blockade can severely limit their utility. In the face of hypotension, sympathetic tone must be maintained in order to assure adequate left ventricular (LV) contractility. Anand I S, Fisher L D, Chiang Y T, et al. *Changes in brain natriuretic peptide and norepinephrine over time and mortality and morbidity in the Valsartan Heart Failure Trial (Val-HeFT).* Circulation 2003; 107:1278-83. Animal studies have demonstrated positive inotropic effects (increased LV pressure and cardiac output without change in systemic vascular resistance) when selectively stimulating certain cardiac efferent sympathetic nerves. Zarse M, Plisiene J, Mischke K, et al. *Selective increase of cardiac neuronal sympathetic tone: a catheter-based access to modulate left ventricular contractility.* J Am Coll Cardiol 2005; 46:1354-9; Meyer C, Rana O R, Saygili E, et al. *Augmentation of left ventricular contractility by cardiac sympathetic neural stimulation.* Circulation 2010; 121:1286-94.

DETAILED DESCRIPTION

The present application discloses methods and systems for treating autonomic imbalance in a patient by energizing a first therapeutic element disposed in a superior vena cava of the patient to deliver therapy to a parasympathetic nerve fiber such as a vagus nerve, and energizing a second therapeutic element disposed within the superior vena cava to deliver therapy to a sympathetic cardiac nerve fiber. A neuromodulation system includes a parasympathetic therapy element adapted for positioning within a blood vessel, a sympathetic therapy element adapted for positioning with the blood vessel; and a stimulator. The stimulator is configured to energize the parasympathetic therapy element to deliver parasympathetic therapy to a parasympathetic nerve fiber disposed external to the blood vessel and energize the sympathetic therapy element within the blood vessel to deliver sympathetic therapy to a sympathetic nerve fiber disposed external to the blood vessel. In disclosed embodiments, delivery of the parasympathetic and sympathetic therapy can be used to decrease the patient's heart rate and while elevating or maintaining the blood pressure of the patient.

Studies conducted by the inventors have elucidated distinct and precise sites in the superior vena cava (SVC) where neurostimulation selectively results in modulation of both cardiac parasympathetic and sympathetic nerves. These anatomic locations were demonstrated using minimally invasive, vascular procedures. These studies demonstrated that independent cardiac parasympathetic and sympathetic stimulation is achievable from fully intravascular locations within the SVC. The results of these studies consistently demonstrated that parasympathetic neuromodulation through vagus nerve stimulation to decrease heart rate (HR) with attendant effect on blood pressure (BP) is simple, straightforward and repeatable. The studies also revealed that sympathetic neuromodulation for the purpose of increasing BP with attendant effect on HR could also be accomplished in a straightforward manner.

The present inventors have achieved rapid, acute parasympathetic and sympathetic modulation of cardiac hemodynamics in humans using intravascular stimulation of the vagus nerve and cardiac sympathetic branches from within the SVC. In those studies, stimulation parameters of 5-15 mA, 20 Hz, and 0.5 ms pulse width were shown to be effective.

Although other investigators have separately stimulated parasympathetic or sympathetic nerves to cardiac effect using surgically-based approaches, no previous approaches have demonstrated simultaneous and selective modulation of both autonomic inputs from intravascular locations. This unprecedented advantage of instantaneous and complete flexibility in management of HR and BP, together with an easy-to-use, minimally invasive approach will provide substantial therapeutic benefit.

The disclosed system can provide a broad spectrum of clinically relevant control through its ability to modulate both HR and BP. In patients that require a decrease in HR and BP, such as those with diastolic heart failure and preserved ejection fraction that present with elevated HR and BP, pure parasympathetic stimulation is provided (lower left hand box of FIG. 1). Similarly, for those patients requiring pure sympathetic stimulation, such as for elevation of heart rate and blood pressure (upper right hand box) the system provides that capability. But in many cases of acute decompensation, particularly in those patients approaching or in cardiogenic shock or with cardiorenal syndrome, pure parasympathetic or pure sympathetic stimulation could have potential detrimental effects. These patients often present with both hypotension and tachycardia. Pure parasympathetic stimulation could worsen this situation by simultaneously decreasing heart rate while potentially reducing blood pressure resulting in inadequate systemic perfusion. On the other hand, pure sympathetic stimulation, while supporting the blood pressure, could further drive the existent tachycardia to extreme levels. Ideally, under the condition of hypotension and tachycardia due to these forms of heart failure, one would want to provide support of the blood pressure to provide for adequate systemic perfusion while simultaneously reducing tachycardia and even lowering the heart rate further to allow adequate cycle length to optimize the stroke volume, preserving or improving cardiac output (upper left hand box), a treatment achievable using the disclosed system.

Ultimately, a combination of autonomic modulation based on hemodynamic feedback of both HR and BP would provide optimal therapy.

While discussed in connection with acute heart failure syndrome, the disclosed system and methods may be used to provide acute autonomic neuromodulation in patients suffering from other conditions, including, but not limited to acute myocardial infarction, pulmonary embolism, hemorrhage, autonomic dysfunction, systemic inflammatory response, syndrome (SIRS), sepsis, as well as post-surgery autonomic dysfunction. Moreover, principles disclosed herein may further be implemented using an implantable system, including one in which the electrodes are chronically disposed or anchored in the SVC at positions determined to deliver the disclosed parasympathetic and/or sympathetic stimulus. An implantable system may have an implantable stimulator, such as one implanted at an intravascular or extravascular (e.g. subcutaneous) site, or a stimulator that is positioned outside the body for wirelessly activating the electrodes. Applications for a chronic system include treatment of patients suffering from chronic heart failure, or autonomic dysfunction associated with other conditions including those listed above.

Figures 1, 2A:
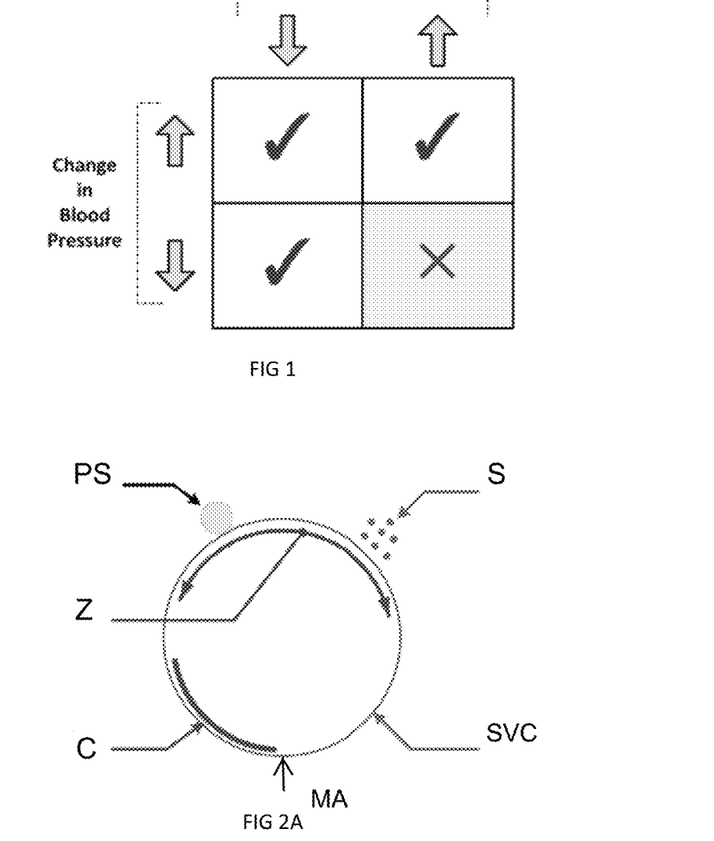
FIG. 1 graphically represents stimulation effects achievable using the disclosed system and method.
FIG. 2A is a top, cross-section view of the superior vena cava illustrating a target electrode region for delivery of therapy to parasypathetic and sympathetic targets.
Figure 2B:
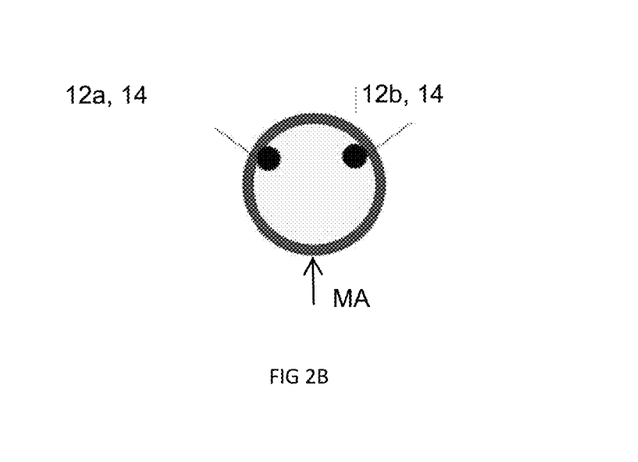
FIG. 2B is similar to FIG. 2A and schematically shows electrodes positioned to deliver therapy to the parasympathetic and sympathetic targets.
Figure 3:
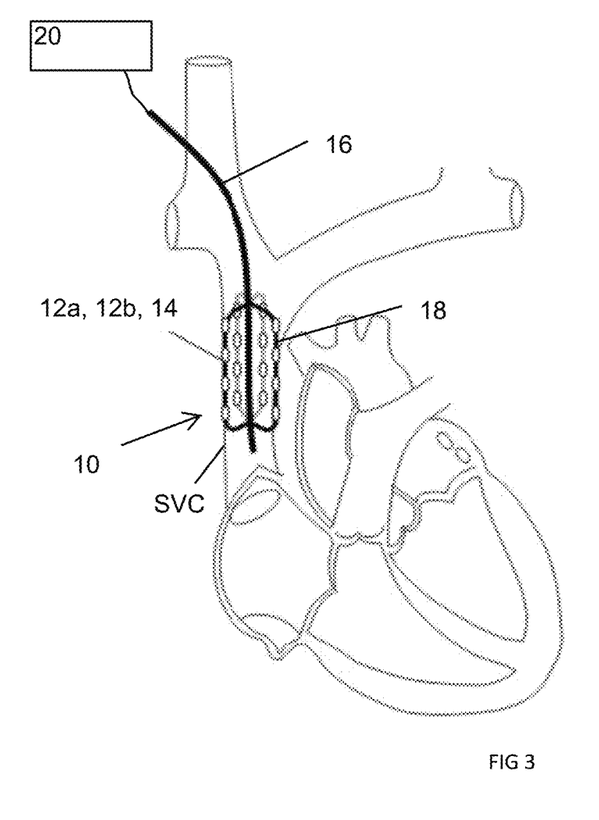
FIG. 3 schematically illustrates a therapy device disposed with the superior vena cava to position electrodes between the superior vena cava's bifurcation and the atrium of the heart.

Accordingly, the present inventors have conceived of a system that is suitable for each type of neuromodulation represented in FIG. 1, including delivery of independent and simultaneous stimulation of parasympathetic and sympathetic cardiac nerves to achieve a simultaneous reduction in HR and increase in BP that results in an increase in cardiac output. Referring to FIG. 3, the neuromodulation system comprises a therapy device 10 having one or more intravascular therapeutic elements 12a, 12b. The therapy device 10 positions the therapeutic elements within the SVC, where they are selectively energized to modulate nerve fibers located outside the vasculature. The therapeutic elements are arranged such that some of the therapeutic elements (referred to herein as the parasympathetic therapeutic elements 12a) direct energy to parasympathetic cardiac nerve fibers from within the SVC, while different ones of the therapeutic elements (referred to as the sympathetic therapeutic elements 12b) direct energy to sympathetic cardiac nerve fibers, also from within the SVC. See FIG. 2B. Because percutaneous advancement of a catheter to the SVC is a simple and straightforward procedure, the ability to position both parasympathetic and sympathetic therapeutic elements within the SVC is highly advantageous.

In preferred embodiments, the therapeutic elements 12a, b are electrodes 14, although it is contemplated that other forms of therapeutic elements (including, but not limited to, ultrasound, thermal, or optical elements) may instead be used. The therapeutic elements are positioned on a flexible therapy device such as a catheter or other flexible elongate carrier 16, allowing advancement of the therapeutic elements from a percutaneous access site to the SVC. The therapy device includes an anchoring structure 18 expandable within the vasculature for biasing the electrodes in contact with the interior surface of the blood vessel so as to optimize conduction of neuromodulation energy from the electrodes to the target nerve fibers.

The therapy device or catheter and its corresponding electrodes and anchoring structure may take a variety of forms. Reference is made to commonly-owned Application Nos. PCT/US12/35712 ("Neuromodulation Systems and Methods for Treating Acute Heart Failure Syndromes"; U.S. Ser. No. 13/547,035, filed Jul. 11, 2012 ("Catheter System for Acute Neuromodulation; each of which is fully incorporated herein by reference. These applications describe exemplary electrode and catheter systems for use in acute neuromodulation which may be used or adapted for use with the disclosed neuromodulation system. Electrodes disclosed in U.S. application Ser. No. 13/281,399 entitled Intravascular Electrodes and Anchoring Devices for Transvenous Stimulation, may also be adapted for use with the disclosed system.

A preferred therapy device for use in the disclosed method utilizes an integrated design, from which stimulus may be directed from a single intravascular therapy device to two or more nerve targets. A device of this type may include a single flexible support 16 or catheter supporting multiple electrodes 18 or electrode arrays which may be independently activated to stimulate a different nerve target. In this type of embodiment, the multiple electrodes (i.e. those used for parasympathetic stimulation and those used for sympathetic stimulation) may be supported by a common support or electrode carrying member 18 that biases the electrodes into contact with the vessel wall. For example, the electrode carrying member 18 might be formed of two or more longitudinal splines carried by the support 16 in an arrangement of the type disclosed in the prior applications incorporated herein (schematically shown in FIG. 3). With this design, the parasympathetic stimulation electrodes may be a bipolar arrangement of electrodes longitudinally arranged on a first spline, and the sympathetic stimulation electrodes may be a bipolar arrangement of electrodes longitudinally arranged on a second spline of the catheter. As another example, the parasympathetic stimulation electrodes and the sympathetic stimulation electrodes may be positioned on a common expandable sleeve formed of mesh, laser cut tubing, or other structures used for endoluminal electrode supports or stents.

The electrode carrying member 18 may include multiple splines or regions having electrode arrays. This arrangement allows a mapping procedure to be conducted upon placement of the catheter within the SVC, such that the splines/regions whose electrodes produce the most optimal parasympathetic and sympathetic response may be determined and used for treatment. In other words, mapping may be used to determine which of multiple electrodes or electrode arrays will be the parasympathetic stimulation electrodes or arrays, and which will be the sympathetic stimulation electrodes or arrays.

In other embodiments, the electrode carrying member supports a first electrode, electrode array, or electrode pair for parasympathetic use, and a second electrode, electrode array, or pair for sympathetic use, together with means for independently or simultaneously adjusting the positions of the first and second arrays during mapping. Other electrode arrangements may be used, including separate catheters (e.g. telescoping or parallel catheters) for sympathetic and parasympathetic stimulation, with each catheter having longitudinally spaced electrodes. In these and the prior examples, independent bipolar electrodes, bipolar electrodes sharing a common pole, or unipolar electrodes may be used—with indifferent electrodes in the unipolar embodiments positioned elsewhere on the catheter or in/on the patient.

An external stimulator 20 energizes the electrodes using stimulation parameters selected to capture the target nerve fibers and to achieve the desired neuromodulation. Suitable stimulation parameters are 5-15 mA, 20 Hz, and 0.5 ms pulse width, although other stimulation parameters may alternatively be used. Feedback to the stimulator is provided by one or more diagnostic sensors. The catheter and stimulator may operate as a closed-loop system, allowing simulation parameters to be automatically determined and/or dynamically controlled in response to information sensed by the sensors and/or derived from sensor feedback. Suitable sensed or derived hemodynamic parameters may include central venous pressure (CVP), pulmonary capillary wedge pressure (PCWP), cardiac index, derivations of vascular resistance, heart rate, blood pressure (arterial). Other parameters may include CO/CI, and cardiac filling pressures. For some parameters such as CVP, feedback may be generated using sensors mounted on the electrode-carrying member or extending through the lumen of its catheter.

Electrode Position

The therapy device 10 positions the electrodes 14 or other therapy elements such that simultaneous sympathetic and parasympathetic stimulation may be carried out using parasympathetic stimulation electrodes disposed in the postero-lateral segment of the mid to cranial portion of the Superior Vena Cava, and sympathetic stimulation electrodes disposed in the postero-medial segment of the mid to cranial portion of the Superior Vena Cava.

In preferred methods, the electrode positions in the SVC from which the parasympathetic (vagus) PS and cardiac sympathetic nerve branches S may be stimulated reside in a zone Z within an approximately 120-270 degree circumferential band centered on the posterior wall of the vessel. In other words, referring to FIG. 2A, if mid-anterior MA is considered to be at 0 degrees (6 o'clock in FIG. 2A below), proceeding clockwise, electrodes may be positioned on the vessel wall within a region that extends along the vessel wall from 45 to 315 degrees. In other embodiments, electrodes may be positioned on the vessel wall within a region that extends along the vessel wall from 120-240 degrees as identified in FIG. 2A. The electrode(s) 12a used for parasympathetic stimulation is/are preferably positioned on the postero-lateral side, and the sympathetic electrode(s) 12b is/are positioned on the postero-medial side as shown in FIG. 2B. In some embodiments, the electrodes are disposed in the same horizontal plane as shown in FIG. 2B, although in other embodiments the electrodes may be longitudinally offset from one another. Stimulation electrodes are preferably positioned away from portions of the SVC wall that are proximate to extravascular nerves whose stimulation would produce undesirable effects. One such collateral stimulation zone C is disposed on the anterior-lateral wall as shown in FIG. 2A.

As shown in FIG. 3, the electrodes 14 are positioned in the portion of the SVC disposed between the SVC's bifurcation and the atrium of the heart.

Control System

Figure 4:
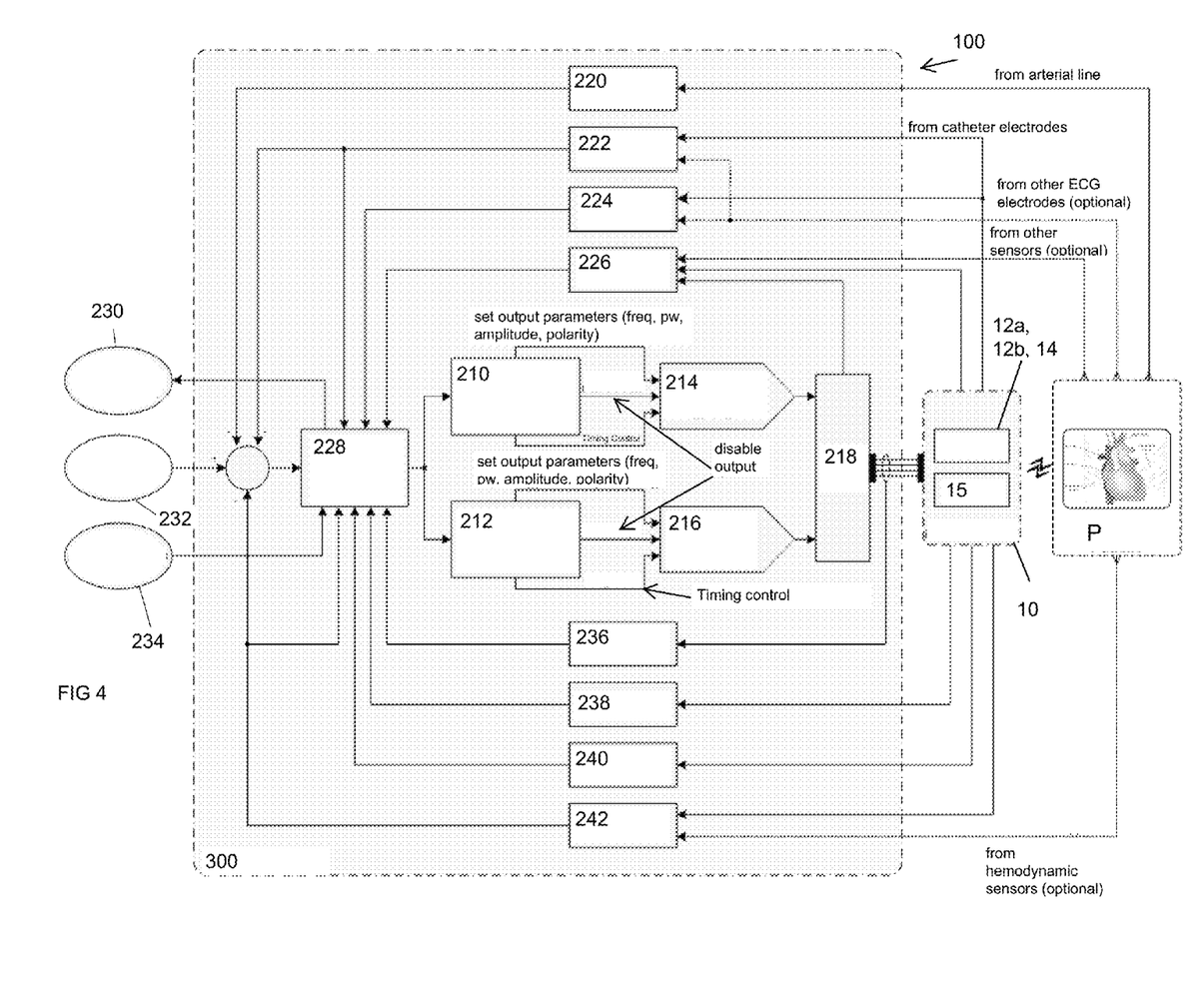
FIG. 4 schematically illustrates an embodiment of a control system for a neuromodulation system.

FIG. 4 schematically illustrates one embodiment of a neuromodulation system, including a control system 100 suitable for carrying out the therapy disclosed herein. The neuromodulation system includes a therapeutic catheter 10 having therapeutic elements 12a, 12b, 14, such as electrode arrays, and optionally, patient and system diagnostic elements; sensors 15 (e.g. pressure sensors, flow sensors, other hemodynamic sensors, other patient condition sensors, and system condition sensors such as position sensors, system connection sensors or other system error condition monitoring sensors). The neuromodulation system also includes an external stimulator, (labeled "NeuroModulator" in the drawing). The external stimulator has a clinician user interface and functions to provide therapeutic stimulation outputs to the therapeutic catheter; therapeutic outputs that are dynamically controlled in a closed-loop manner in response to information from one or more of the diagnostic elements. The diagnostic elements include sensors for patient hemodynamic feedback such as heart rate (HR), blood pressure (BP), and other suitable sensed or derived hemodynamic parameters (which may include central venous pressure (CVP), pulmonary capillary wedge pressure (PCWP), cardiac index, derivations of vascular resistance, cardiac output, and cardiac filling pressures); sensors and/or analyzers to determine other patient conditions such as cardiac arrhythmia, cardiac capture, respiration, or patient movement; and other sensors and analyzers to monitor system conditions for error, malfunction or unsafe state (referred to as "safety monitoring") that should be indicated to the clinician and/or result in termination of stimulation. Together, these system components form a control system that is capable of safely balancing both parasympathetic and sympathetic tone to achieve the clinically desired HR and BP conditions, just as in the native autonomic nervous system.

Figure 5:
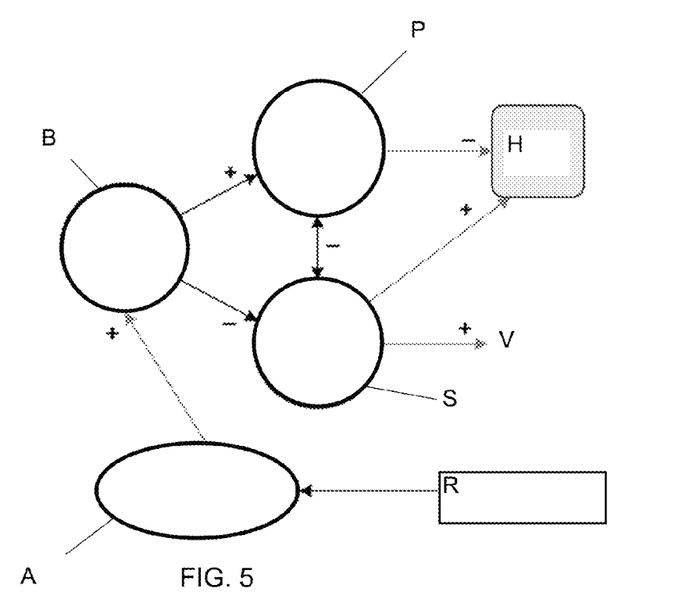
FIG. 5 is a graphical representation illustrating control of normal cardiovascular function by the autonomic nervous system's cardiovascular control system.
Figure 6:
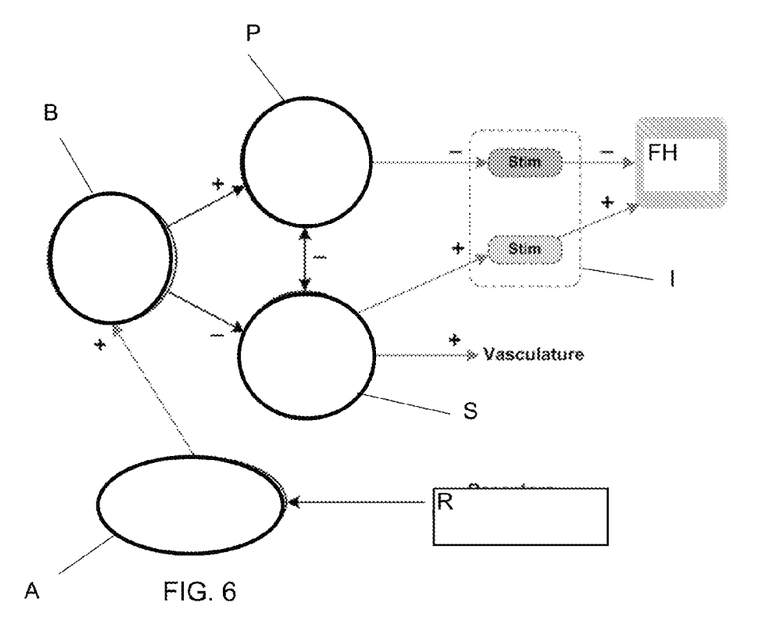
FIG. 6 is a graphical representation illustrating an adjusted cardiovascular control system achieved through the addition of the disclosed neuromodulation system to the autonomic nervous system's cardiovascular control system.

The unique advantage of this autonomic system modulation is the utilization of simultaneous and selective modulation of both parasympathetic and sympathetic inputs directly to the heart from distinct sites completely in the vasculature, but ideally within a common blood vessel. The complete flexibility in the management of HR and BP in combination with a minimally invasive, percutaneous approach to access the direct autonomic inputs to the heart provides a substantial advantage in the treatment of clinical conditions such as acute heart failure syndrome (AHFS). Normal cardiovascular function is controlled by the autonomic nervous system's cardiovascular control system, a negative feedback system, in which increased BP and cardiac output increases afferent activity which inhibits sympathetic activity and activates parasympathetic activity, while decreased BP and cardiac output decreases afferent activity, resulting in the opposite effect, as shown in FIG. 5. In FIGS. 5 and 6, the following references are used: B (brain), P (parasympathetic activity), S (sympathetic activity), H (heart), FH (failed heart), A (afferents, sensory inputs), R (receptors, throughout the system), V (vasculature), I (adjusted inputs to heart), stim (stimulation).

In the case of decompensated heart failure, however, since the heart is damaged, the effective transfer function of the heart is perturbed, as cardiac output is depressed despite higher HR which leads to decompensation of the entire cardiovascular system, and the negative feedback cardiovascular control system can no longer function appropriately. The failing heart is being driven with sympathetic excitation due to the lowered BP and cardiac output sensed by the afferent nerves, which leads to further diminished cardiac output—effectively, the system now operates at a point of decompensation due to the changed transfer function of the failing heart. The neuromodulation system has the ability to alter the inputs directly at the heart in an immediate, minimally invasive manner so that the failing heart can be controlled in a manner more suitable for its current condition. This immediately changes the operating point of the cardiovascular control system to a clinically appropriate point, where treatment of the acute decompensation, such as with inotropic agents or diuresis, can be safely conducted with the autonomic system operating at a more suitable state. The addition of the neuromodulation system allows a new, adjusted cardiovascular control system as depicted in FIG. 6. Furthermore, the closed-loop control options afforded by simultaneous and selective parasympathetic and sympathetic stimulation allows the neuromodulation system to adapt as the patient's condition improves and the operating point of the system moves away from the decompensated state. The neuromodulation system can then minimize its contribution to the heart's direct neural inputs as the system begins functioning more normally.

Utilizing this control system, the neuromodulation system provides two primary functions: a continuous safety-monitored, closed-loop control to modulate heart rate (HR) and blood pressure (BP) with user-specified boundaries for the ultimate purpose of controlling patient hemodynamics; and an automatic parasympathetic and sympathetic response mapping function for the ultimate purpose of selecting the ideal electrodes to stimulate target nerves.

The control system, shown in FIG. 4, contains a Parasympathetic Control 210 function, a Sympathetic Control function 212, a Safety Monitoring function 228, a Parasympathetic Stimulation Output function 214, a Sympathetic Stimulation Output function 216, an Electrode Switching function 218, and a number of other system feedback elements, consisting of sensors, analyzers and detectors of various system and patient conditions. The control system elements or functions can be implemented individually as or any combination of electronic circuitry, computer subsystems, computer software, mechanical subsystems, ultrasound subsystems, magnetic subsystems, electromagnetic subsystems, optical subsystems, and a variety of sensors or detectors including, but not limited to, electromechanical sensors, electrochemical sensors, thermal sensors, and infrared sensors. The control system elements or functions communicate with each other by direct physical means (electrically wired connection, mechanical interaction) or other indirect means (such as wireless RF, visible light, infrared, sound, ultrasound).

The Parasympathetic and Sympathetic Output functions generate the therapeutic stimuli that can be, but are not limited to, electrical pulses. These two output functions can generate independent therapeutic levels (for example, electrical currents, voltages, and pulse widths), timing (frequencies, triggers or gates to other timing such as ECG events, the latter of which might be used, for example, to initiate stimulation during the atrial refractory period), and polarity (as applicable). The two output functions allow independent parasympathetic and sympathetic therapeutic outputs to be generated and delivered to the therapy catheter's therapeutic elements, described as electrodes.

The Electrode Switching function 218 provides the means to connect the Parasympathetic and Sympathetic Output functions to the desired electrodes on the therapy catheter's electrode array so as to capture the target cardiac nerves fibers (i.e., the parasympathetic nerve fibers to the Parasympathetic Output function and the sympathetic nerve fibers to the Sympathetic Output function). The selection of which connection or connections to make is determined during the response mapping procedure, described later in this application.

The Parasympathetic and Sympathetic Control functions implement the system's overall function based on user inputs 232 (target HR and BP boundaries, or immediate output disable 234) and feedback from patient sensed or hemodynamic parameters, as well as system diagnostic conditions for safety monitoring. The Parasympathetic and Sympathetic Control functions directly govern the therapeutic output from Parasympathetic and Sympathetic Output functions, respectively, by controlling the therapeutic levels, timing, polarity, as well as the ability to disable the outputs. The Control functions are responsible for, at a minimum, the two primary functions of the neuromodulation system: the closed-loop modulation of HR and BP, as well as the response mapping function. In one example, the Parasympathetic and Sympathetic Control functions implement closed loop modulation utilizing the user-targeted HR and BP boundaries, as well as the feedback from actual HR and BP. Also, in other examples, additional sensed and/or derived hemodynamic parameters (such as flow rates, cardiac output, etc. described above) can also be determined by the system and used in addition to, or in place of, HR and BP. The transfer function implemented by the Parasympathetic and Sympathetic Control functions can be linear or non-linear in nature. For example, although the HR and BP feedback response may be linear within a given range of modulation, non-linear response may occur at other points. Also, an input from the Safety Monitoring function may require a non-linear response to protect patient safety.

The Safety Monitoring function 228 receives inputs from the various patient and system diagnostic functions for the purpose of monitoring the safety of the system. The Safety Monitoring function can output to the Parasympathetic and Sympathetic Control functions to alter the therapeutic outputs to the patient and/or initiate a clinician alarm or indicator 230. The purpose of these outputs is to ensure that the neuromodulation system's therapeutic outputs are providing stimulation to the patient only when the system believes the state of the patient and system monitored conditions are in a known defined state, described in this applications as "safe". For example, a patient condition that may be monitored by the Safety Monitoring function is the presence of inadvertent atrial capture by the therapeutic neurostimulation. This state would be undesirable from a clinical perspective because the therapeutic stimulation intended for nerve capture is capturing myocardium, and the Safety Monitoring function would, in this example, communicate to the immediately disable the therapeutic output from the system. Another example of a patient condition would be the cardiac ECG to control the timing of the therapeutic outputs with respect to the cardiac cycle such as synchronizing stimulation to the heart. Another example of a patient condition would be any suitable sensed or derived hemodynamic parameter (such as flow rates, cardiac output, etc. described above) that is clinically unsafe and should result in either an alarm or disabling of therapeutic output. There are also a variety of system conditions that shall be monitored by the Safety Monitoring function, including, but not limited to, a connection failure to the therapy catheter, monitoring central venous pressure to determine if the therapy catheter position is anatomically correct, and an external stimulator malfunction (such as electrical circuit failure, computer malfunction, software malfunction, mechanical malfunction, etc.) Any system condition that can be sensed or derived from the system's sensors is monitored by the Safety Monitoring function.

The neuromodulation system also contains patient and system feedback elements that sense, measure or derive various patient and system conditions and provide this information to both the Parasympathetic and Sympathetic Control functions and the Safety Monitoring function. These feedback elements include sensors on the therapy catheter 10 such as pressure sensors, flow sensors, thermal sensors, PO2 sensors, mechanical interacting component, magnetic components, as well as the therapeutic electrodes and additional sensing electrodes. In addition, clinical sensors used directly on the patient such as arterial pressure transducers, ECG electrodes, and other hemodynamic monitors can be utilized and connected to the external stimulator. For example, feedback of arterial blood pressure and heart rate are key to the performance of the neuromodulation system. An Arterial Blood Pressure Sensor function 220 that would be connected to a standard arterial line pressure transducer can be utilized to determine BP and HR for the control system. Therapy catheter electrodes or surface ECG electrodes can be connected to an ECG Analyzer function 222 that would derive ECG parameters such as HR, P and R-wave timing, refractory timing, and presence of cardiac arrhythmias, such as tachycardia or fibrillation, can be utilized as inputs to the system or for safety monitoring. Other Hemodynamic Sensors 242 can be used to sense or derive hemodynamic parameters (such as flow rates, cardiac output, temperature, PO2 etc. described above) can be used both for closed-loop control, as well as safety monitoring. A Central Venous Pressure Sensor 240 is disclosed to provide feedback both on the therapy catheter's position, as well as hemodynamic feedback that can be utilized as part of the closed-loop control system. A Cardiac Capture Detector function 224 can be utilized to check if the neuro stimulation therapy is unintentionally capturing the atrium due to incorrect catheter position and may induce arrhythmia. A Catheter Connection Detector 236 that is comprised of, for example, a magnetic or proximity sensor can be used to assure the therapy catheter and external stimulator connection integrity, and a Catheter Position Sensor 238 can be utilized to assure that the catheter anatomic placement is stable during system usage. Other Safety Monitoring Sensors 226 may also be provided throughout the system to detect malfunctions (such as electrical circuit failure, computer malfunction, software malfunction, mechanical malfunction, etc.) or other unsafe.

Method

An exemplary method for using an integrated device to achieve hemodynamic control will next be described. This method is particularly useful for decreasing heart rate and increasing or maintaining blood pressure in the treatment of acute heart failure syndrome.

First, the integrated catheter is percutaneously delivered to the superior vena cava (e.g. using access through the femoral vein, subclavian, or internal jugular vein). The electrode carrying member is positioned in the SVC between the bifurcation and the top of the atrium, and the electrodes are brought into contact with the surrounding walls of the SVC, preferably such that the electrodes contact the posterior wall of the SVC. Electrode contact is preferably achieved by expanding the electrode carrying member within the SVC, as described in the prior applications incorporated herein.

Mapping is performed to identify the optimal electrode location. This mapping may be either manually controlled by the clinician or automatically controlled utilizing the external stimulator and electrode carrying members on the catheter. Where the electrode carrying member supports multiple arrays of electrodes, each array is independently energized and the response measured until the optimal array for the parasympathetic stimulation is identified and until the optimal array for the sympathetic stimulation is identified. Where the electrode carrying member supports a single array for parasympathetic use and a single array for sympathetic use, the arrays are energized and the response measured. The arrays may be repositioned and the test repeated until the optimal positions for the parasympathetic and sympathetic arrays are identified. In either case, mapping includes a parasympathetic mapping step in which electrodes on the postero-lateral segment of the SVC are energized, and a sympathetic mapping step in which electrodes on the postero-medial segment of the SVC are energized.

During the parasympathetic mapping step, heart rate is monitored prior to and then during energization of the electrodes disposed on the SVC's postero-lateral segment. If the heart rate during stimulation does not decrease by at least a threshold amount, for example at least 5%, a second parasympathetic site is selected by repositioning the parasympathetic array or by energizing another array located on the postero-lateral wall of the SVC. The process is repeated until a stimulation site is determined that will decrease the heart rate by at least the threshold amount (which in this example is 5%).

During the sympathetic mapping step, heart rate and/or blood pressure is monitored prior to and during energization of the electrodes on the postero-medial segment. If the heart rate and/or blood pressure during stimulation does not increase by at least a threshold amount, for example 5%, a second sympathetic site is selected by repositioning the sympathetic array or by energizing another array located on the postero-medial wall of the SVC. The process is repeated until a stimulation site is determined that will increase the blood pressure by at least the threshold amount (which in this example is 5%). Note that even where the desired therapy is to lower HR and sustain or elevate BP, identification of a target sympathetic stimulation site might still include monitoring for an increase in heart rate by at least a threshold amount during energization of the electrodes being positioned for sympathetic stimulation. This is because an elevation in heart rate during sympathetic mapping confirms that sympathetic cardiac nerves are being captured by the sympathetic side stimulus.

The parasympathetic and sympathetic mapping steps may be performed simultaneously or separately. Where each of these steps is performed separately, during the sympathetic mapping step, the electrodes on the postero-lateral segment of the SVC are preferably not energized, and likewise during the parasympathetic mapping step electrodes on the postero-medial segment of the SVC are preferably not energized. An alternative sympathetic mapping step, which is performed after the parasympathetic stimulation site has been identified, involves conducting sympathetic mapping while simultaneously delivering parasympathetic stimulation from the identified parasympathetic stimulation site. In this example, a sympathetic electrode site might be chosen that allows the patient's blood pressure to be maintained despite the decreased HR associated with the parasympathetic stimulation.

Mapping may further include adjusting the stimulation parameters (e.g. amplitude, frequency and pulse width) and observing the response while the electrodes remain at a given electrode location so as to identify the optimal stimulation parameters.

In some embodiments, mapping is automatic, such that the user sets the target heart rate and blood pressure values and the system selects the stimulation parameters and/or electrode position based on the measured response to stimulus during mapping.

Once the parasympathetic and sympathetic electrodes are determined to be in suitable positions to achieve the desired stimulation of the target nerves, treatment is initiated. The parasympathetic and sympathetic electrodes may be energized simultaneously, or the parasympathetic and sympathetic stimulation may be alternated. Where the parasympathetic and sympathetic therapeutic energy is delivered at separate times, it may occur at separate times asynchronously to each other, or separately, but synchronized to each other The stimulation parameters for the parasympathetic and sympathetic electrodes may be the same or they may be different.

For treatment of acute heart failure syndrome, the neuromodulation may be used to lower the patient's heart rate and raise or maintain the patient's blood pressure. Target heart rates fall in a range of 30-180 beats per minute (bpm), preferably 45-140 bpm, and most preferably 60-100 bpm. Target systolic blood pressures, with the patient in a supine position, fall in a range of 70-180 mmHg, preferably 80-150 mmHg, and most preferably 90-120 mmHg.

By providing simultaneous stimulation of parasympathetic nerves and sympathetic cardiac nerve fibers, the system may operate such that stimulation of one system (e.g. the parasympathetic or sympathetic nervous system) augments or mollifies the other system in a manner that produces the desired physiologic outcome. One particular benefit of such a system is its ability to respond to detection of a diminished physiological response resulting from adaptation of the autonomic nervous system (ANS) to a particular set of stimulation parameters. For example, in use the system is set up to deliver parasympathetic and sympathetic stimulations to produce a desired range of heart rate and blood pressure. It is recognized that there are various combinations of the sympathetic and parasympathetic stimulus that will achieve the target heart rate and blood pressure ranges. As the body adapts to the particular combination of stimuli being delivered by the system, the system will sense a diminution of the physiological response, and will thus begin to apply a different combination of parasympathetic and sympathetic stimulation that will produce the target HR and BP ranges. Alternatively, the system may be programmed to periodically shift from one combination of parasympathetic and sympathetic stimulation parameters to another combination, so as to avoid adaptation by the ANS. Where the catheter includes multiple electrode arrays, the system might further be programmed to periodically alter which of the arrays is used to deliver stimulus, as yet another safeguard against adaptation.

Referring again to FIG. 1 above, the system may alternatively be operated to decrease both heart rate and blood pressure by solely or primarily energizing the parasympathetic electrodes. One suitable application for this mode is the treatment of tachycardia. In another mode of operation, the pulse generator is used to solely or primarily energize the sympathetic electrodes in order to increase blood pressure, such as for treatment of hypotension.

While in this application use of the sympathetic stimulation has focused on use of the sympathetic stimulation to maintain or elevate blood pressure, in other alternative methods sympathetic electrodes in the SVC may instead be used to stimulate sympathetic cardiac nerves that are primarily associated with chronotropic or dromotropic effects.

Experimental Results

In an experimental arrangement, separate catheters were positioned in the SVC at the positions described in the preceding paragraphs. Stimulus was delivered at 20 Hz, Pulse Width=0.5 ms, and Amplitude of 10 mA for each catheter. Stimulus was performed on each catheter simultaneously from electrodes (4 mm separation) in a vertical plane. The distance between the two catheters was about 1-2 cm and at an estimated 45 degrees circular.

As discussed above, similar electrode arrangements can be achieved through a variety of different catheter designs, including but not limited to electrode placement on the splines of a catheter of the type described in the incorporated applications, allowing the parasympathetic stimulation electrodes and the sympathetic stimulation electrodes to reside on a single catheter and yet to be placed at distinct, separate, areas for the optimal stimulation of parasympathetic and the sympathetic nerves. The figures discussed above illustrate the positioning of such a catheter with the SVC.

The animal study was designed to evaluate the hemodynamic effects of simultaneously modulating both parasympathetic and sympathetic cardiac efferent nerves via intravascular stimulation at distinct sites in the superior vena cava (SVC).

In an initial study using two canines, a 12Fr sheath was placed via the Seldinger technique in the right femoral vein and a second 12Fr sheath was positioned in left femoral vein. Separate sheaths were employed in these experiments in order to maximize stability and minimize interaction between catheters. A 7Fr and 6Fr sheath were introduced into the right and left femoral arteries, respectively. Arterial access allowed left ventriculogram acquisition and continuous BP monitoring. Two guide catheters containing 8Fr standard quadripolar stimulation catheters were introduced from the femoral veins and employed to identify the optimal region for parasympathetic and sympathetic stimulation in the SVC, which was easily achieved. Once the stimulation site was located, the catheters were maintained in the same position for the duration of the study.

In both canine subjects, dual channel, simultaneous neurostimulation was applied to each catheter. Stimulation durations of approximately 1-2 minutes were repeated to assure reproducibility of hemodynamic effect. Pharmacologic intervention intended to block parasympathetic effect was also administered during stimulation (Atropine, 0.5 mg IV).

Based on the findings from the first canine experiment, the second canine experiment was modified to include increased time period continuous stimulation, measurement of ejection fraction, and the use of beta blockade (propranolol) to confirm sympathetic stimulation effect. Therefore, the second canine was subjected to continuous dual channel stimulation for 1 hour with continuous monitoring. Also, in the second canine, the Atropine was followed 5 minutes later by beta-blocker propranolol (3 mg IV for two doses). Finally, in the second canine, a pigtail catheter was placed in the left ventricle and ventriculograms for the purpose of measuring ejection fraction obtained at baseline and during dual stimulation.

The first canine experiment (Test #1) resulted in the finding that the novel, fully intravascular, simultaneous, dual channel stimulation of both parasympathetic and sympathetic cardiac efferent nerves can be achieved, and results in remarkable HR decrease together with BP elevation. Also, administration of Atropine confirmed that the resulting HR decrease was solely due to the parasympathetic stimulation.

The second canine experiment (Test #2) easily confirmed the same findings as seen in Test #1, in addition to successful 1 hour continuous stimulation, an increase in ejection fraction, and the use of beta blockade confirmed sympathetic stimulation effect.

Three additional canine experiments were then conducted to confirm the findings as seen in the first two experiments. The same procedure was utilized, and in addition, direct cardiac output measurements were taken in Tests #4 and Test #5 utilizing an invasive flow measurement catheter.

The five consecutive canine experiments provided consistent confirmation that independent control of HR and BP was achieved. In particular, lower HR simultaneous with higher BP was consistently demonstrated. The effects were demonstrated acutely and over the course of an hour. Ejection fraction and cardiac output were improved. Targeted drug use demonstrated the target neuromodulation effects.

The animal study was designed to evaluate the hemodynamic effects of simultaneously modulating both parasympathetic and sympathetic cardiac efferent nerves via intravascular stimulation at distinct sites in the superior vena cava (SVC). The experimental results are summarized as follows:

In all five (5) canines, parasympathetic stimulation-only resulted in a significant decrease in HR with attendant effects on BP and sympathetic stimulation-only demonstrated an increase in HR and BP as seen in earlier studies In all five (5) canines, simultaneous parasympathetic and sympathetic dual stimulation resulted in a decrease of HR and an increase or maintenance in BP After cessation of stimulation, all five canines returned to baseline hemodynamic parameters within 1-3 minutes In two of two canines in which the measurement was taken, the ejection fraction improved measurably during dual stimulation In two of two canines in which the measurement was taken, the cardiac output was preserved or improved measurably during dual stimulation despite the reduction in HR In four of four canines in which the measurement was taken, the HR and BP response was maintained for 1 hour of stimulation and when stimulation was discontinued, the HR returned to baseline within 10 seconds with baseline BP returning within 1-3 minutes In all five (5) canines, Atropine administration eliminated stimulation-induced HR reduction confirming selective parasympathetic modulation Also, in four of four canines in which the measurement was taken, propranolol administration mitigated stimulation-induced BP response confirming selective sympathetic modulation The results of the five canine studies are set forth in Table 1 below:

TABLE 1

Stimulation Data

| Test # | | Parasympathetic Stim | Sympathetic Stim | Dual Stim | Dual Stim (after 1 hour) | Atropine Effect | Propranolol Effect |
|---|---|---|---|---|---|---|---|
| 1 | Δ HR | ↓87 bpm | ↑2 bpm | ↓87 bpm | | ✓ | |
| | | ↓52% | ↑1% | ↓53% | | | |
| | Δ BP | ↑7 mmHg | ↑24 mmHg | ↑25 mmHg | | | |
| | | ↑4% | ↑15% | ↑16% | | | |
| 2[i] | Δ HR | ↓63 bpm | ↑3 bpm | ↓35 bpm | ↓46 bpm | ✓ | ✓ |
| | | ↓47% | ↑3% | ↓26% | ↓35% | | |
| | Δ BP | ↓6 mmhg | ↑25 mmHg | ↑35 mmHg | ↑29 mmHg | | |
| | | ↓3% | ↑31% | ↑36% | ↑27% | | |
| 3 | Δ HR | ↓94 bpm | ↑39 bpm | ↓58 bpm | ↓79 bpm | ✓ | ✓ |
| | | ↓61% | ↑26% | ↓37% | ↓48% | | |
| | Δ BP | ↓35 mmHG | ↑18 mmHg | ↑31 mmHg | ↑14 mmHg | | |
| | | ↓16% | ↑9% | ↑14% | ↑7% | | |
| 4[ii] | Δ HR | ↓53 bpm | ↑11 bpm | ↓54 bpm | ↓44 bpm | ✓ | ✓ |
| | | ↓35% | ↑7% | ↓38% | ↓30% | | |
| | Δ BP | ↓3 mmHg | ↑16 mmHg | ↑14 mmHg | ↑50 mmHg | | |
| | | ↓1% | ↑7% | ↑7% | ↑23% | | |
| 5[iii] | Δ HR | ↓48 bpm | ↑60 bpm | ↓44 bpm | ↓25 bpm | ✓ | ✓ |
| | | ↓38% | ↑55% | ↓34% | ↓19% | | |
| | Δ BP | ↓23 mmHg | ↑13 mmHg | ↑30 mmHg | ↑29 mmHg | | |
| | | ↓11% | ↑7% | ↑15% | ↑14% | | |

[i]Ejection Fraction: No stim = 67%, with stim = 72%
[ii]Ejection Fraction: No stim = 41%, with stim = 55% Cardiac Output: No stim = 4.6 L/min, with stim = 5.1 L/min
[iii]Cardiac Output: No stim = 5.9 L/min, with stim = 6.8 L/min

We claim:

1. A method of treating autonomic imbalance in a patient having a heart rate and a blood pressure, comprising:
    delivering neuromodulation therapy to sustain or increase the blood pressure while decreasing the heart rate, said neuromodulating therapy including
        (a) stimulating at least one extravascular parasympathetic nerve fiber using at least one first intravascularly-positioned electrode; and
        (b) stimulating at least one extravascular cardiac sympathetic nerve fiber using at least one second intravascularly-positioned electrode,
    wherein said method includes placing the second electrode in a posterior portion of a blood vessel.

2. The method of claim 1, further including introducing a therapy device into the vasculature, the therapy device having the first and second electrodes thereon, and advancing the therapy device within the vasculature to position the first and second electrodes within the vasculature.

3. The method of claim 1, wherein at least one of the first and second electrodes is disposed in venous vasculature superior to the heart.

4. The method of claim 3, wherein at least one of the first and second electrodes is disposed in the superior vena cava.

5. The method of claim 1, wherein steps (a) and (b) are performed simultaneously.

6. The method of claim 1 wherein steps (a) and (b) are performed at separate times.

7. The method of claim 1, wherein the at least one parasympathetic nerve fiber is a vagus nerve fiber.

8. The method of claim 1, wherein the at least one sympathetic nerve fiber is a sympathetic cardiac nerve fiber.

9. The method of claim 1, wherein the method includes positioning the first and second electrodes in a segment of the superior vena cava extending between a right atrium and a junction of brachiocephalic veins.

10. The method of claim 1, further including energizing the first and second electrodes using a stimulator disposed external to the patient.

11. The method of claim 1, further including monitoring blood pressure and heart rate of the patient, and modifying stimulus from the first and second electrodes in response to detected changes in heart rate and/or blood pressure.

12. The method of claim 1 further including independently controlling stimulation of the sympathetic and parasympathetic nerve fibers.

13. The method of claim 1, wherein step (b) is performed with the second electrode in said posterior position.

* * * * *